(12) United States Patent
Silverman et al.

(10) Patent No.: US 9,670,141 B2
(45) Date of Patent: Jun. 6, 2017

(54) (S)-3-AMINO-4-(DIFLUOROMETHYLENYL) CYCLOPENT-1-ENE-1-CARBOXYLIC ACID, AND RELATED COMPOUNDS AS GABA AMINOTRANSFERASE INACTIVATORS FOR THE TREATMENT OF EPILEPSY, ADDICTION AND HEPATOCELLULAR CARCINOMA

(71) Applicant: NORTHWESTERN UNIVERSITY, Evanston, IL (US)

(72) Inventors: Richard B. Silverman, Winnetka, IL (US); Kenji Takaya, Osaka (JP); Hoang V. Le, Evanston, IL (US); Jose I. Juncosa, Salisbury, MD (US)

(73) Assignee: NORTHWESTERN UNIVERSITY, Evanston, IL (US)

( * ) Notice: Subject to any disclaimer, the term of this patent is extended or adjusted under 35 U.S.C. 154(b) by 0 days.

(21) Appl. No.: 15/289,480

(22) Filed: Oct. 10, 2016

(65) Prior Publication Data
US 2017/0101364 A1    Apr. 13, 2017

Related U.S. Application Data

(60) Provisional application No. 62/239,330, filed on Oct. 9, 2015.

(51) Int. Cl.
*C07C 229/48*     (2006.01)
*A61K 31/205*     (2006.01)
*A61K 31/196*     (2006.01)

(52) U.S. Cl.
CPC ................... *C07C 229/48* (2013.01)

(58) Field of Classification Search
None
See application file for complete search history.

(56) References Cited

U.S. PATENT DOCUMENTS

6,794,413 B1 *   9/2004   Silverman ............ A61K 31/557
                                              514/573

FOREIGN PATENT DOCUMENTS

WO      2008-023364 A1    2/2008

OTHER PUBLICATIONS

Lippert, et al., "4-Amino-hex-5-enoic Acid, a Selective Catalytic Inhibitor of 4-Aminobutyric-Acid Aminotransferase in Mammalian Brain", Eur. J. Biochem, vol. 74, No. 3; Apr. 15, 1977; pp. 441-445.
Dewey et al., "A Novel Strategy for the Treatment of Cocaine Addiction", Synapse, vol. 30, No. 2, Oct. 1998; pp. 119-129.
Dewey et al., "A Pharmacologic Strategy for the Treatment of Nicotine Addiction", Synapse, vol. 31, No. 1, Jan. 1999; pp. 76-86.
Gerasimov et al., "Gamma-Vinyl GABA Inhibits Methamphetamine, Heroin, or Ethanol-Induced Increases in Nucleus Accumbens Dopamine", Synapse, vol. 34, No. 1, Oct. 1999; pp. 11-19.
Pan et al., "Design, Synthesis, and Biological Activity of a Difluoro-Substituted, Conformationally Rigid Vigabatrin Analogue as a Potent ?-Aminobutyric Acid Aminotransferase Inhibitor", Journal of Medicinal Chemistry, vol. 46, No. 25, Dec. 4, 2003; pp. 5292-5293.
International Search Report and Written Opinion of the International Searching Authority, corresponding to International Application No. PCT/US2016/056245, dated Jan. 26, 2017; 16 total pages.
Lu, et al., "Fluorinated Conformationally-Restricted ?-Aminobutyric Acid Aminotransferase Inhibitors", Journal of Medicinal Chemistry, E-Pub, vol. 49, No. 25, Oct. 11, 2006; pp. 7404-7412 and Figures 1-2.
Kanth et al., "QSAR Analysis of a Few GABA Aminotransferase Inhibitors as Potent Antiepileptics", Indian Journal of Chemistry, vol. 44B, Mar. 2005; pp. 595-599.
Chebib et al., "The Effects of Cyclopentane and Cyclopentene Analogues of GABA at Recombinant GABAC Receptors", European Journal of Pharmacology, vol. 430, No. 2-3; Nov. 2001; pp. 185-192.

* cited by examiner

*Primary Examiner* — Brian J Davis
(74) *Attorney, Agent, or Firm* — Carter, DeLuca, Farrell & Schmidt, LLP

(57) ABSTRACT

Cyclopentene carboxylic acid-related compounds as GABA-AT inhibitors for treatment of various addictions, disorders and disease states.

42 Claims, 11 Drawing Sheets

Time and dose dependent inactivation of GABA-AT by 1

Secondary plot of $k_{obs}$ against inactivator concentrations

Figure 6A
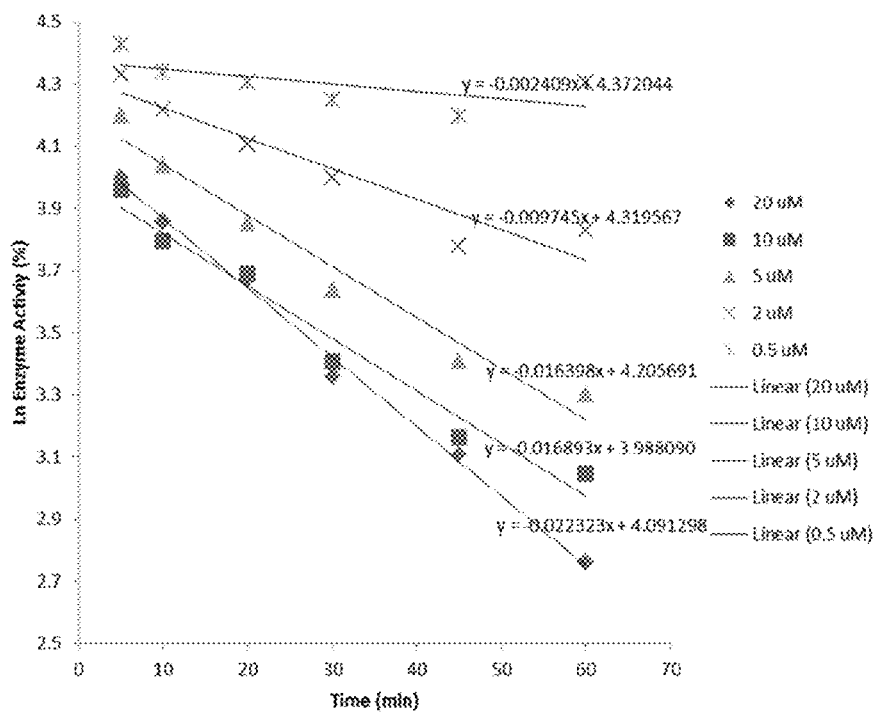
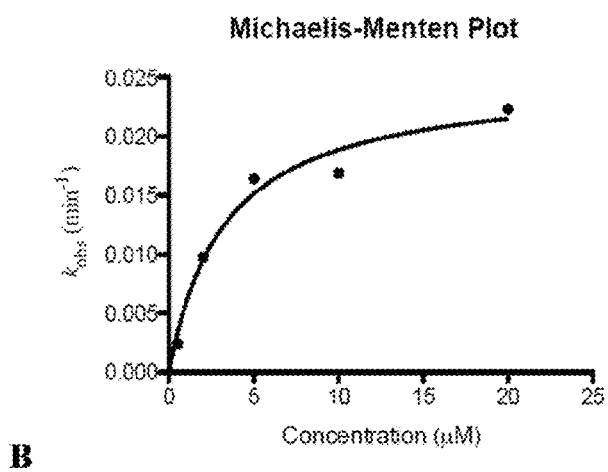
Figure 6B

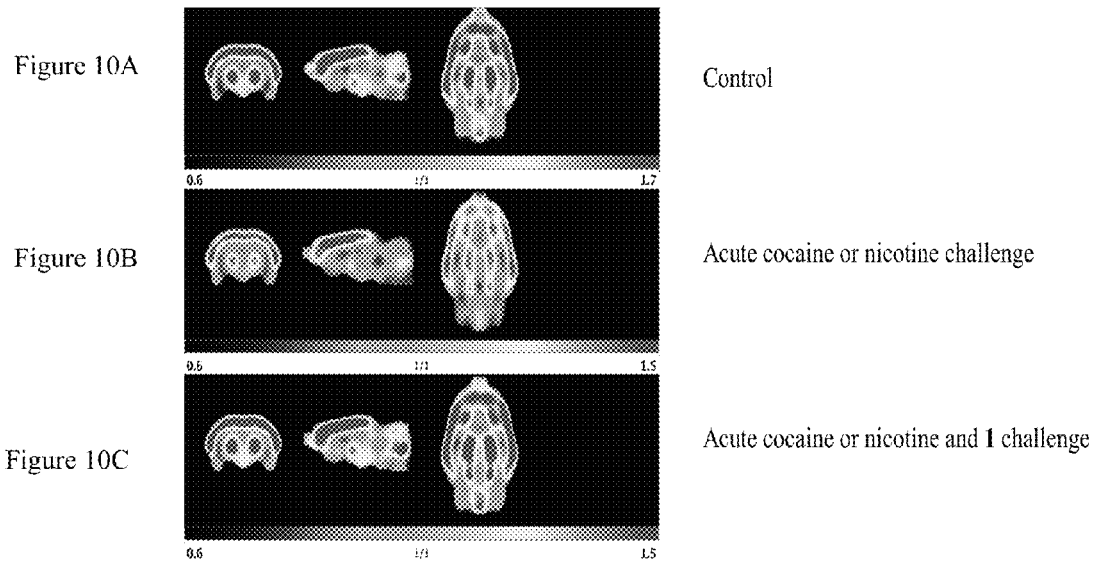
Figure 10A — Control
Figure 10B — Acute cocaine or nicotine challenge
Figure 10C — Acute cocaine or nicotine and 1 challenge Figure 11A    Figure 11B
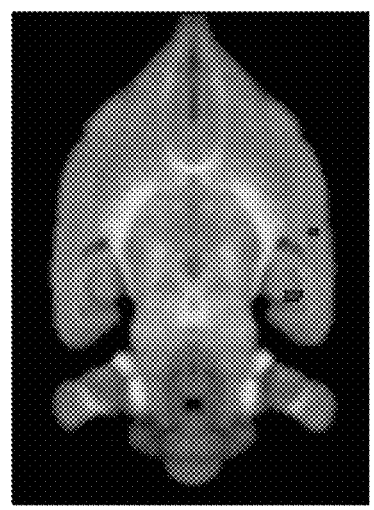
Cocaine    Bregma -7.20 mm    Cocaine + 1

(S)-3-AMINO-4-(DIFLUOROMETHYLENYL) CYCLOPENT-1-ENE-1-CARBOXYLIC ACID, AND RELATED COMPOUNDS AS GABA AMINOTRANSFERASE INACTIVATORS FOR THE TREATMENT OF EPILEPSY, ADDICTION AND HEPATOCELLULAR CARCINOMA

This application claims priority to and the benefit of application Ser. No. 62/239,330 filed Oct. 9, 2015, the entirety of which is incorporated herein by reference.

This invention was made with government support under R01 DA030604 awarded by the National Institutes of Health. The government has certain rights in the invention.

BACKGROUND OF THE INVENTION

γ-Aminobutyric acid (GABA), the major inhibitory neurotransmitter in the central nervous system, is released from presynaptic inhibitory neurons and binds to chloride-selective ion channel receptors ($GABA_A$ and $GABA_C$) and to G-protein coupled receptors ($GABA_B$) to hyperpolarize the postsynaptic membrane, thereby controlling neuronal activity downwardly. Low levels of GABA are linked to many neurological disorders, including epilepsy, Parkinson's disease, Alzheimer's disease, Huntington's disease, and cocaine addiction.

Gabaergic drugs are those that improve secretion or transmission of GABA. These drugs as a family have been used to treat a wide variety of nervous system disorders including fibromyalgia, neuropathy, migraines related to epilepsy, restless leg syndrome, and post traumatic distress disorder. Gabaergic drugs include $GABA_A$ and $GABA_B$ receptor ligands, GABA reuptake inhibitors, GABA aminotransferase inhibitors, GABA analogs, or molecules containing GABA itself.

In 1998 a novel strategy was developed for the treatment of cocaine addiction by inhibiting the activity of γ-aminobutyric acid aminotransferase (GABA-AT), the pyridoxal 5'-phosphate (PLP)-dependent enzyme that degrades GABA. GABA-AT inhibition raises GABA levels, which antagonizes the rapid release of dopamine in the nucleus accumbens (NAcc), a neurochemical response to cocaine and other drugs of abuse. Since then, vigabatrin, the only FDA-approved inactivator of GABA-AT, which is currently used as an antiepilepsy drug, has been successful in the treatment of addiction in animal models for cocaine, nicotine, methamphetamine, heroin, and alcohol. Vigabatrin also was effective in the treatment of cocaine addiction in humans, with up to 28% of patients achieving abstinence in a 9-week double-blind trial. The potential of vigabatrin for general therapeutic use, however, may be problematic because permanent vision loss has been reported to arise from its long-term administration in 25-40% of epilepsy patients.

Recently, (1S,3S)-3-amino-4-difluoromethylenyl-1-cyclopentanoic acid, now called CPP-115, was designed, synthesized and found to be 186 times more efficient in inactivating GABA-AT than vigabatrin. (Pan, Y.; Qiu, J.; Silverman, R. B. *J. Med. Chem.* 2003, 46 (25), 5292-5293.) When tested in a multiple-hit rat model of infantile spasms, CPP-115 suppressed spasms at doses>100-fold lower than those used with vigabatrin and produced longer spasm suppression. CPP-115 also had a much larger margin of safety and a considerably lower retinal toxicity liability than vigabatrin. When tested in freely moving rats after administration of 20 mg/kg cocaine, CPP-115 was >300 times more potent than vigabatrin in reducing the release of dopamine in the NAcc. (Silverman, R. B. *J. Med. Chem.* 2012, 55 (2), 567-575; Pan, Y.; Gerasimov, M. R.; Kvist, T.; Wellendorph, P.; Madsen, K. K.; Pera, E.; Lee, H.; Schousboe, A.; Chebib, M.; Brauner-Osborne, H.; Craft, C. M.; Brodie, J. D.; Schiffer, W. K.; Dewey, S. L.; Miller, S. R.; Silverman, R. B. *J. Med. Chem.* 2012, 55 (1), 357-366). Also, administration of CPP-115 at 1 mg/kg, along with cocaine, to cocaine-addicted rats, showed a similar effect in eliminating their addictive behavior as vigabatrin at 300 mg/kg with cocaine.

Originally, CPP-115 was designed to inactivate GABA-AT via a Michael addition mechanism that would lead to a covalent adduct with the enzyme. However, it was later discovered that CPP-115 inactivates the enzyme by forming a tightly-bound complex with the enzyme via strong electrostatic interactions of the two carboxylate groups in the resulting metabolite with Arg192 and Arg445 in the active site (Scheme 1). (Lee, H.; Doud, E. H.; Wu, R.; Sanishvili, R.; Juncosa, J. I.; Liu, D.; Kelleher, N. L.; Silverman, R. B. *J. Am. Chem. Soc.* 2015, 137 (7), 2628-2640). Metabolism is initiated by Schiff base formation of CPP-115 with the lysine-bound PLP, followed by γ-proton removal and tautomerization, resulting in a Michael acceptor. However, before Lys-329 can attack this Michael acceptor, catalytic hydrolysis of the difluoromethylenyl group occurs, leading to the PLP-bound dicarboxylate metabolite, which undergoes a conformational change and tightly binds to Arg192 and Arg445 (Scheme 1). However, molecular modeling indicates a movement of the difluoromethylenyl group upon tautomerization, which bends away from Lys-329, making it too far for nucleophilic attack (Scheme 1). Instead, the enzyme presumably catalyzes hydrolysis of the difluoromethylenyl group.

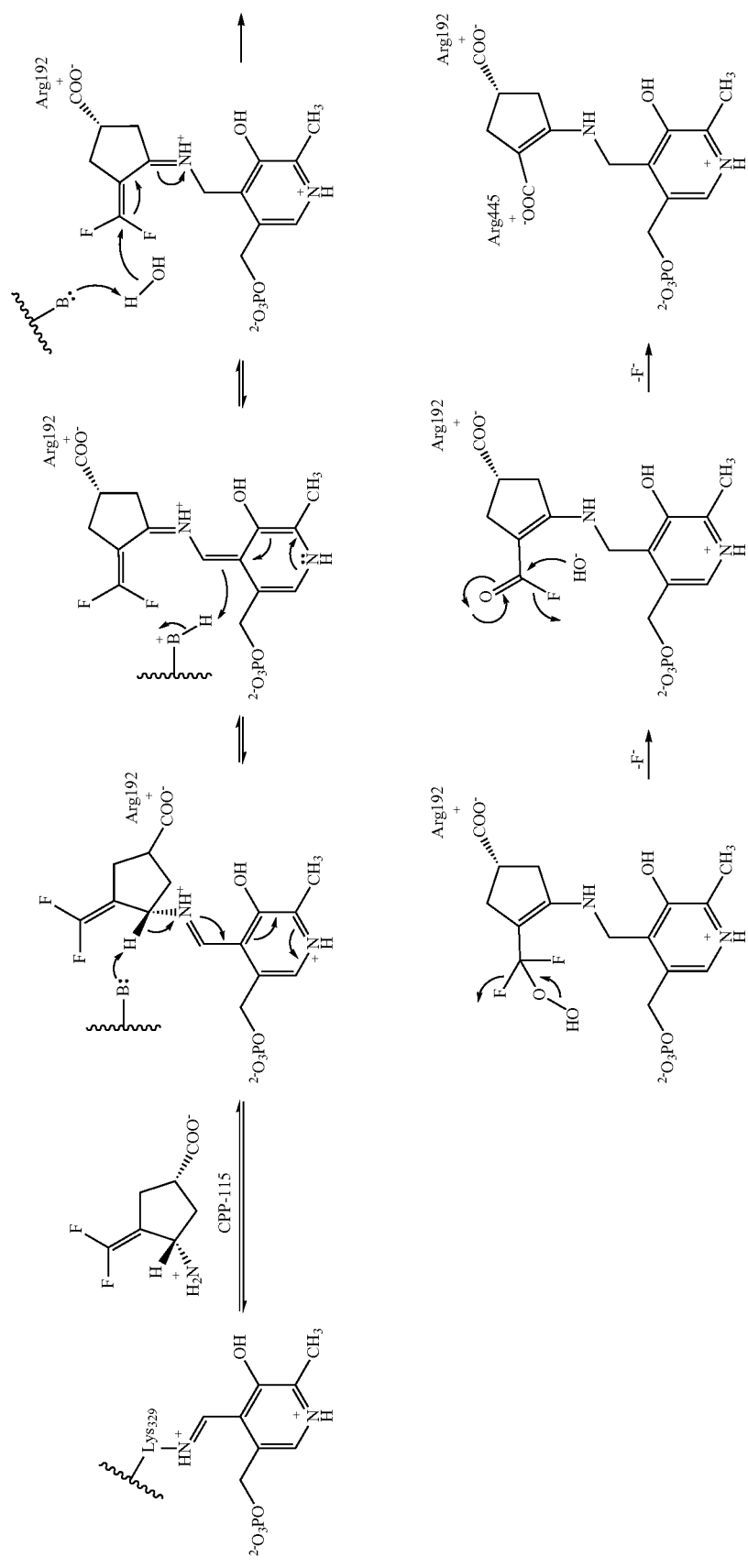
Scheme 1. Mechanism of Inactivation of GABA-AT by CPP-115

SUMMARY OF THE INVENTION

In light of the foregoing, it is an object of the present invention to provide compounds, compositions and related methods of use for the selective inhibition of GABA-AT, thereby overcoming various deficiencies and shortcomings of the prior art including those outlined above. It would be understood by those skilled in the art that one or more aspects of this invention can meeting certain objectives, while one or more other aspects can meet certain other objectives. Each objective may not apply equally, in all its respects, to every aspect of this invention. As such, the following objects can be viewed in the alternative with respect to anyone aspect of this invention.

It can be an object of the present invention to provide one or more small molecule, non-peptide compounds exhibiting selective aminotransferase inhibition.

It can be another object of the present invention to provide one or more such compounds for in vitro use and study under conditions indicative of one or more mammalian disease states.

Alternatively, it can also be an object of the present invention to provide one or more such compounds enabling in vivo treatment of such disease states.

It can also be an object of the present invention, alone or in conjunction with one or more of the foregoing objects, to provide a compound or composition for GABA-AT inactivation, inhibition or modulation and/or treatment of an addiction and associated indications.

It can also be an object of the present invention, alone or in conjunction with one or more of the foregoing objects, to provide a compound or composition for OAT inactivation, inhibition or modulation and/or treatment of a malignant pathologic proliferative disorder, including without limitation hepatocellular carcinoma.

It can also be an object of the present invention, alone or in conjunction with one or more of the foregoing objects, to provide a compound or composition for treatment of a range of neurological or psychological disorders, including but not limited to those described elsewhere herein.

Other objects, features, benefits and advantages of the present invention will be apparent from this summary and the following descriptions of certain embodiments of such compounds, compositions and/or methods and will be readily apparent to those skilled in the art having knowledge of the synthetic techniques described herein. Such objectives, features, benefits and advantages will be apparent from the above as taken into conjunction with the accompanying examples, data, figures and references incorporated herein, together with all reasonable inferences to be drawn therefrom.

In part, the present invention can be directed to a compound of a formula

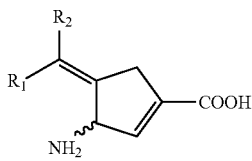

wherein $R_1$ and $R_2$ can be independently selected from H, F, Cl, Br and I, where at least one of $R_1$ and $R_2$ is not H, or a salt of such a compound. Without limitation, in certain embodiments, the stereocenter comprising an amino substituent can have an (S) stereochemical configuration.

In part, the present invention can be directed to a compound of a formula

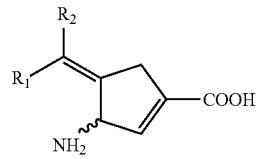

wherein $R_1$ and $R_2$ can be selected from H and F, and at least one of $R_1$ and $R_2$ can be F, or a salt of such a compound. In certain embodiments, $R_1$ and $R_2$ can be F. Without limitation, in certain such embodiments, the stereocenter comprising an amino substituent can have an (S) stereochemical configuration.

In part, the present invention can be directed to a compound of a formula

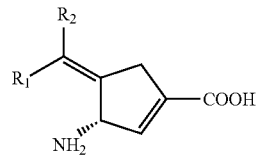

wherein $R_1$ and $R_2$ can be selected from H and F, and at least one of $R_1$ and $R_2$ can be F, or a salt of such a compound. In certain non-limiting embodiments, $R_1$ and $R_2$ can be F.

Regardless, compounds of or useful in conjunction with this invention are without stereochemical or configurational limitation. As illustrated and discussed below, such compounds and/or their intermediates are available as single enantiomers or racemic mixtures from which isomers can be resolved. Accordingly, any stereocenter can be (S) or (R). As a separate consideration, with respect to mono-substituted methylenyl embodiments, such compounds can have either a Z or E configuration. As another separate consideration, various compounds can be present as an acid salt, either partially or fully protonated. In certain such embodiments, with respect to an ammonio substituent, the counter ion can be a conjugate base of a protic acid. In certain such or other embodiments, with respect to a carboxylate substituent, the counter ion can be an alkaline, alkaline-earth or ammonium cation. Further, it will be understood by those skilled in the art that any one or more the compounds of this invention can be provided as part of a pharmaceutical composition comprising a pharmaceutically-acceptable carrier component for use in conjunction with a treatment method or medicament.

In part, the present invention can be directed to a method of reducing, inhibiting, modulating or otherwise affecting GABA-AT activity. Such a method can comprise providing a compound of a formula

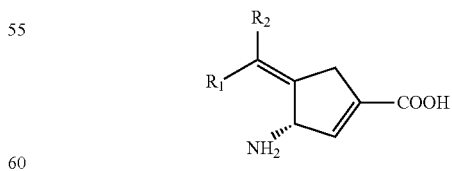

wherein $R_1$ and $R_2$ can be independently selected from H, F, Cl, Br and I, where at least one of $R_1$ and $R_2$ is not H, or a salt of such a compound; and contacting such a compound with a medium comprising a γ-aminobutyric acid aminotransferase, such a compound as can be in an amount sufficient to reduce, inhibit, modulate or otherwise affect such aminotransferase activity. Such a method can thereby bind such a compound to and/or inactivate such an aminotransferase and raise or modulate γ-aminobutyric acid levels in such a medium. Such contact can be in vitro or in vivo. Alternatively, this invention can be considered as a method for the treatment of low levels of γ-aminobutyric acid in a subject in need thereof. Regardless, in certain non-limiting embodiments, $R_1$ and $R_2$ can be F.

In part, the present invention can also be directed to a method of inhibiting, modulating, blocking or otherwise affecting release or elevation of dopamine responsive to ingestion of an addictive substance. Such a method can comprise providing a compound a formula

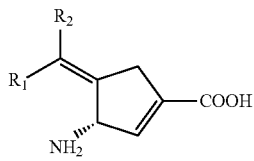

wherein $R_1$ and $R_2$ can be selected from H and F, and at least one of $R_1$ and $R_2$ can be F, or a salt of such a compound; and contacting such a compound with a cellular medium comprising a γ-aminobutyric acid aminotransferase, such a compound in an amount sufficient to modulate or inhibit dopamine levels responsive to ingestion of such an addictive substance or to an addictive behavior. Such a method can thereby increase γ-aminobutyric acid levels and modulate and/or control dopamine levels. Alternatively, this invention can be considered as a method for the treatment of excessive dopamine release in a subject challenged by addiction and/or otherwise in need thereof. Regardless, in certain non-limiting embodiments, $R_1$ and $R_2$ can be F.

In part, the present invention can also be directed to a method for the treatment of substance addiction, for instance and without limitation, cocaine, heroin, alcohol, barbiturates, amphetamines, cannabis, methadone, opioids, stimulants and nicotine addiction and combinations thereof, in a mammalian subject in need thereof. Such a method can comprise administering to such a subject a compound of a formula

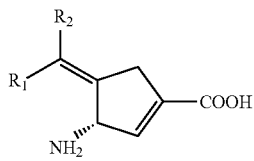

wherein $R_1$ and $R_2$ can be selected from H and F, and at least one of $R_1$ and $R_2$ can be F, or a salt of such a compound, such a compound as can be in an amount sufficient to increase γ-aminobutyric acid levels and/or modulate/control dopamine levels in the hippocampus of a subject having ingested, for instance, cocaine, heroin, alcohol, barbiturates, amphetamines, cannabis, methadone, opioids, stimulants and nicotine and combinations thereof. Such a method can thereby reduce hippocampal glucose metabolism. In certain non-limiting embodiments, $R_1$ and $R_2$ can be F.

In part, the present invention can be directed to a method of reducing, inhibiting, modulating or otherwise affecting OAT activity. Such a method can comprise providing a compound of a formula

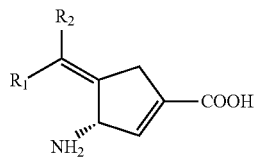

wherein $R_1$ and $R_2$ can be independently selected from H, F, Cl, Br and I, where at least one of $R_1$ and $R_2$ is not H, or a salt of such a compound; and contacting such a compound with a medium comprising an ornithine aminotransferase, such a compound as can be in an amount sufficient to reduce, inhibit, modulate or otherwise affect such aminotransferase activity. Such contact can be in vitro or in vivo. Regardless, in certain non-limiting embodiments, $R_1$ and $R_2$ can be F.

In part, the present invention can also be directed to a method of reducing activity of an ornithine aminotransferase expressed by a human hepatocellular carcinoma. Such a method can comprise providing a compound a formula

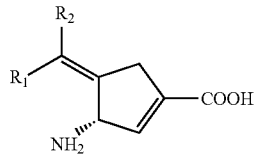

wherein $R_1$ and $R_2$ can be selected from H and F, and at least one of $R_1$ and $R_2$ can be F, or a salt of such a compound; and contacting such a compound with a cellular medium comprising a hepatocellular carcinoma expressing an ornithine aminotransferase, such a compound as can be in an amount sufficient to modulate or reduce ornithine aminotransferase activity. Such a method can thereby reduce glutamate production in such a medium. Regardless, in certain non-limiting embodiments, $R_1$ and $R_2$ can be F.

In part, the present invention can also be directed to a method for the treatment of psychological and neurological disorders. Such a method can comprise administering to a mammalian subject in need thereof a compound of a formula

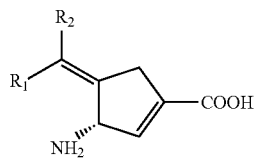

wherein $R_1$ and $R_2$ can be selected from H and F, and at least one of $R_1$ and $R_2$ can be F, or a salt of such a compound, such a compound as can be in an amount sufficient to increase γ-aminobutyric acid levels in such a subject. Without limitation, psychological and neurological disorders can be selected from those discussed elsewhere herein. Regardless, in certain non-limiting embodiments, $R_1$ and $R_2$ can be F.

BRIEF DESCRIPTION OF THE DRAWINGS

FIGS. 6A-B. (A) Time- and concentration dependent inhibition of OAT by 1. The natural logarithm of the percentage of remaining OAT activity was plotted against the preincubation time at each inhibitor concentration to obtain the $k_{obs}$ (slope) value for each concentration. $k_{obs}$ is the rate constant describing the inactivation at each inhibitor concentration. (B) Michaelis-Mentel plot for 1. The $k_{obs}$ values were fitted using a nonlinear regression analysis to obtain the inhibition constant ($K_I$) and the rate constant of enzyme inactivation ($k_{inact}$).

FIGS. 10A-C. PET digital images of control (A); and effects of cocaine or nicotine (B) and an acute dose of 1 and cocaine or nicotine (C) on $^{11}$C-raclopride uptake.

FIGS. 11A-B. Statistical parametric map of PET digital images showing the effects of (A) cocaine and (B) cocaine and 1 on increased metabolic demands in the hippocampus.

DETAILED DESCRIPTION OF CERTAIN EMBODIMENTS

Figure 1:
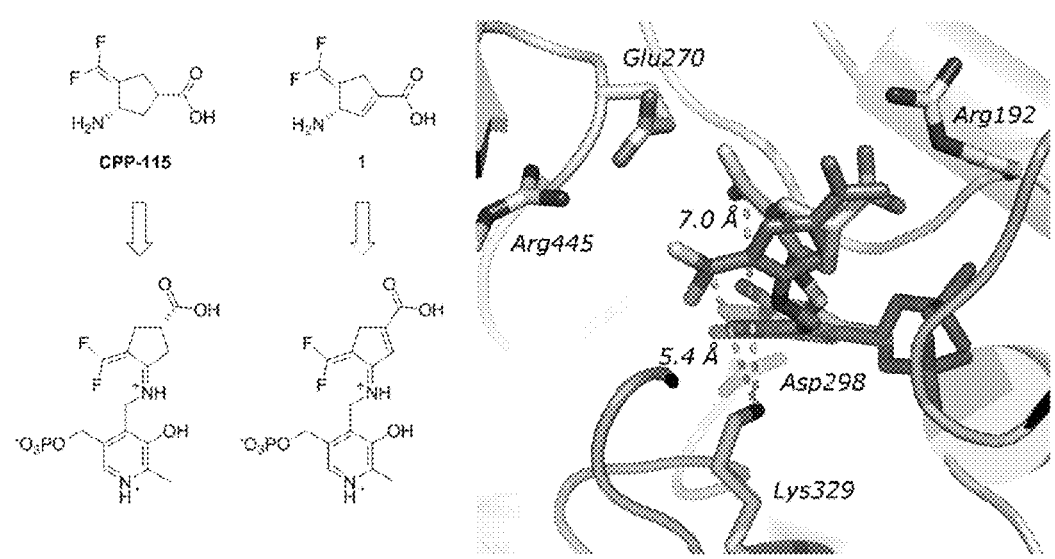
FIG. 1. In silico model of the PLP-CPP-115 adduct (right) and the PLP-1 adduct (left) after tautomerization, as well as key nearby residues.

As relates to certain embodiments of this invention, computer modeling with GABA-AT indicated that, unexpectedly, the difluoromethylenyl group of CPP-115 would be closer to Lys-329 after tautomerization if the cyclopentane ring conformation was locked by installation of an endocyclic double bond (5.4 Å for 1 vs 7.0 Å with CPP-115, FIG. 1). Accordingly, the present invention is directed to (S)-3-amino-4-(difluoromethylenyl)cyclopent-1-ene-1-carboxylic acid (1), and structural variations thereof, its biological evaluation with GABA-AT and non-GABAergic off-targets, and its in vivo activity in freely moving rats with regard to the release of dopamine in the NAcc, as well as its effect on neuronal glucose metabolism.

The synthesis of 1 is shown in Scheme 2, starting from CPP-115 hydrochloride. The carboxylic acid and amino groups were first protected, and then the α-proton to the methyl ester was deprotonated by KHMDS, followed by the addition of phenyl selenyl chloride, resulting in a 7:3 inseparable mixture of diastereomers (4). The protecting groups were removed to afford 6. It was found that the purity of 6 was crucial for the final purity of 1. Oxidative elimination of the phenylselenyl group in 6 under mild conditions gave a clean 10:6 isomeric mixture of 1 and 2. Many attempts to separate 1 from 2 by chromatography were unsuccessful, but it was discovered in the process that 2 was less stable than 1. A strategy to selectively modify and remove the more reactive 2 using a soft thiol nucleophile (2-mecaptobenzoic acid) was developed successfully. After the reaction was confirmed as complete by $^{19}$F NMR, C-18 reverse phase column chromatography was used to afford pure 1. Various other compounds of this invention and/or useful in conjunction therewith can be prepared from the corresponding 3-amino-4-methylenylcyclopentane-1-carboxylic acids using synthetic techniques of the sort provided in Scheme 2 or straight-forward variations thereof, as would be understood by those skilled in the art and made aware of this invention.

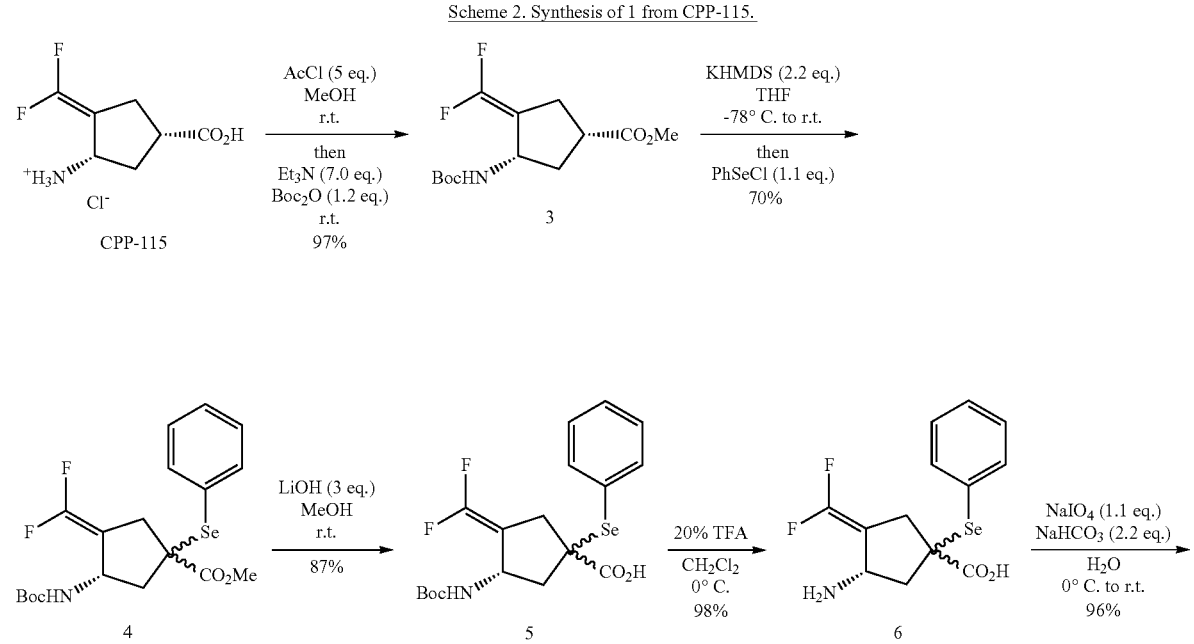

Scheme 2. Synthesis of 1 from CPP-115.

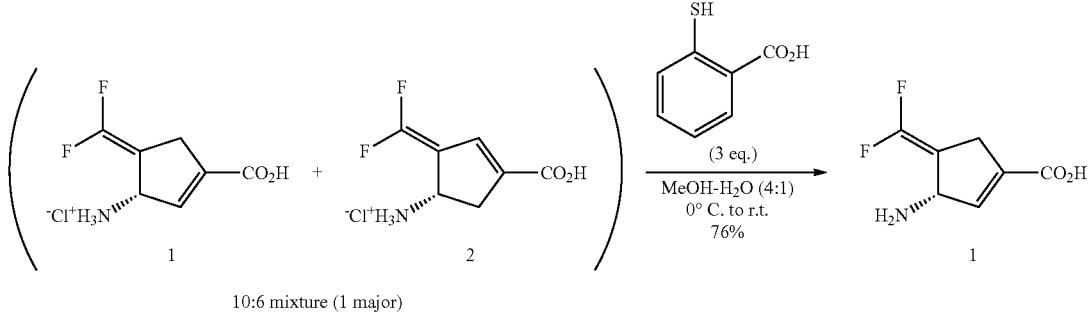

10:6 mixture (1 major)

Figure 2A:
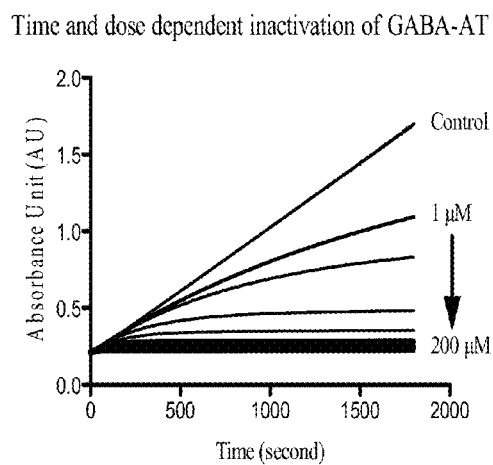
FIGS. 2A-B. (A) Time- and concentration dependent inhibition of GABA-AT by 1. (B) Secondary plot of $k_{obs}$ against concentration to determine $k_{inact}$ and $K_I$ values of 1.
Figure 2B:
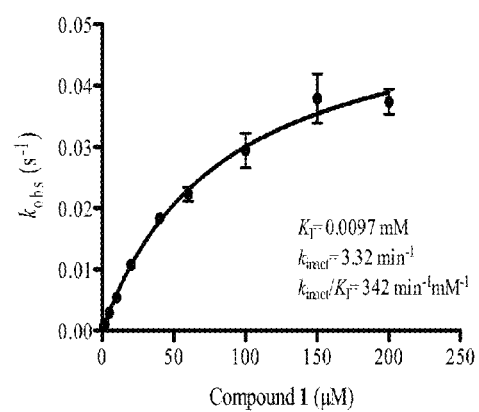

Preliminary in vitro results showed that 1 was an exceedingly potent inactivator of GABA-AT. Because the inactivation occurred so rapidly, the inhibition constant ($K_I$) and the rate constant of enzyme inactivation ($k_{inact}$) for the inactivation of GABA-AT by 1 could not be determined accurately using a conventional Kitz and Wilson replot, even under nonoptimal conditions, as reported originally for CPP-115. Instead, a recently developed progress curve analysis method was used to measure the kinetic constants (FIG. 2), which allowed measurements under optimal conditions (Salminen, K. A.; Leppänen, J.; Venäläinen, J. I.; Pasanen, M.; Auriola, S.; Juvonen, R. O.; Raunio, H. Drug Metab. Dispos. 2011, 39 (3), 412-418). The same method was used to measure the kinetic constants of CPP-115 as a reference. The results showed that 1 had a higher binding affinity to GABA-AT than CPP-115 ($K_I$ values of 1 and CPP-115 were 9.7 μM and 59 μM, respectively), and 1 inactivated GABA-AT at a greater rate than CPP-115 ($k_{inact}$ values of 1 and CPP-115 were 3.32 min$^{-1}$ and 2.05 min$^{-1}$, respectively). Overall, the efficiency constant for 1 ($k_{inact}/K_I$=342 mM$^{-1}$ min$^{-1}$) is 9.8 times larger than that for CPP-115 ($k_{inact}/K_I$=34.9 mM$^{-1}$ min$^{-1}$); therefore, 1 is 9.8 times more efficient as an inactivator of GABA-AT than CPP-115.

Figure 3A:
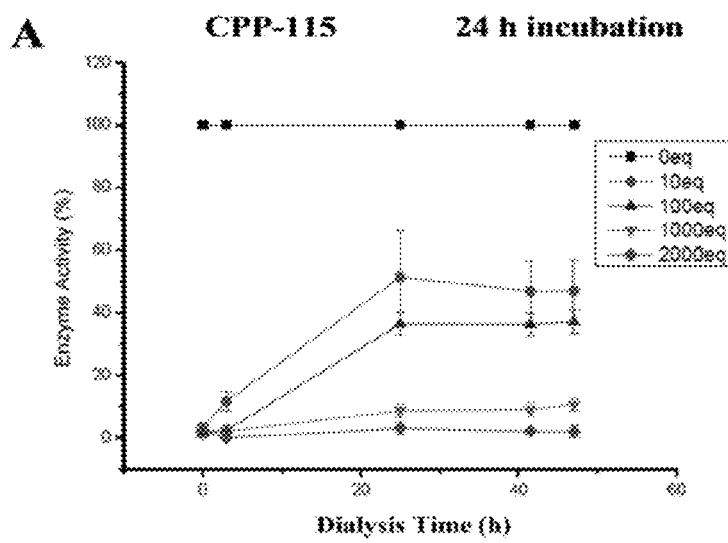
FIGS. 3A-B. Reactivation of inactivated GABA-AT by CPP-115 after 24 h incubation (A) and 1 after 4 h incubation (B).
Figure 3B:
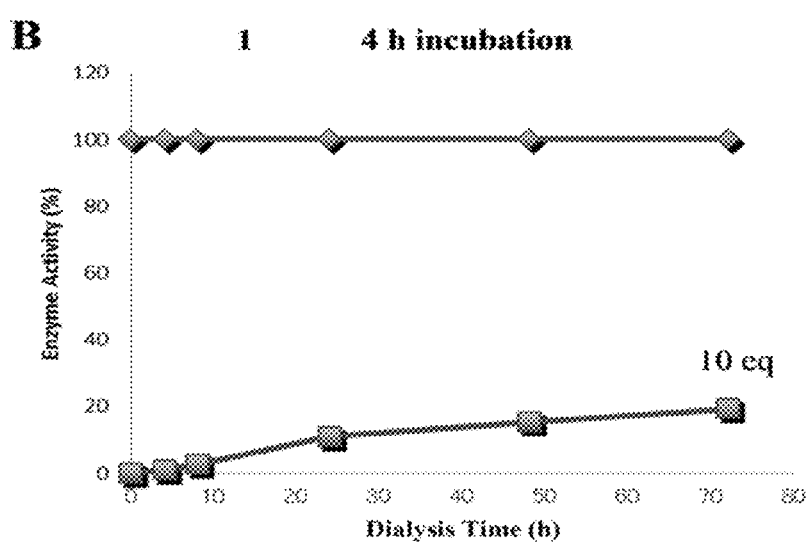

Because 1 was designed to form an irreversible covalent bond with Lys-329, time-dependent reactivation of GABA-AT was conducted to test if the mechanism involved irreversible and/or reversible inhibition. After GABA-AT was completely inactivated by 10 equiv of 1 with 4 h incubation, the inactivated enzyme was dialyzed and aliquots at different time intervals were collected and assayed for return of enzyme activity. After 72 h of dialysis, the enzyme activity of 1-inactivated GABA-AT partially returned and stabilized at 20% (FIG. 3B). The same time-dependent reactivation of GABA-AT was previously conducted on CPP-115; when GABA-AT was completely inactivated by 100 equiv of CPP-115 with 24 h incubation and then dialyzed, the enzyme activity returned to 40% (FIG. 3A). Even at 10 times the concentration and much longer incubation time, CPP-115 was much less efficient than 1 at inactivating GABA-AT. The return of a small amount of enzyme activity from 1-inactivated GABA-AT indicates that inactivation may include both an irreversible component and a reversible component.

Figure 4:
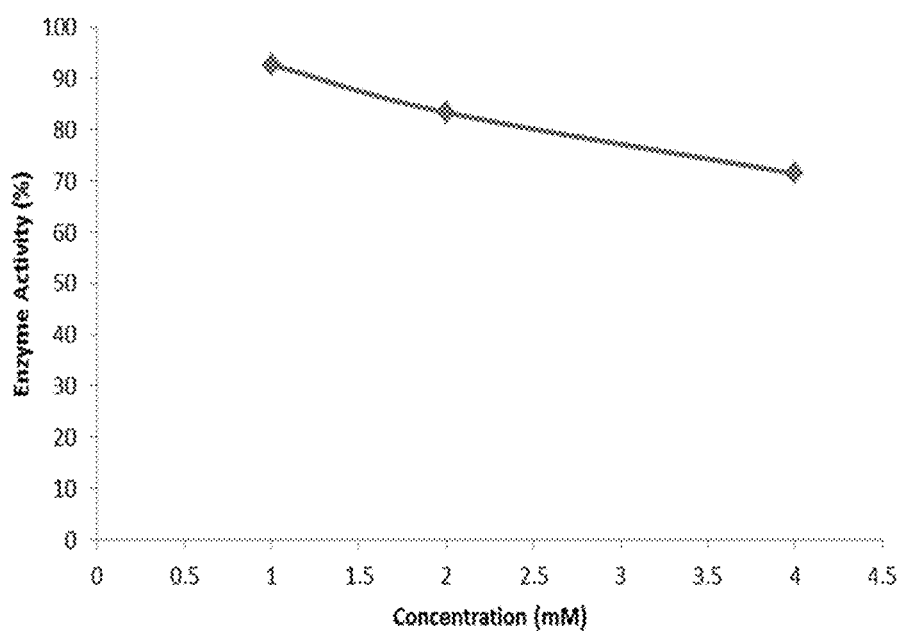
FIG. 4. Concentration Dependent Inhibition of Asp-AT by 1.
Figure 5:
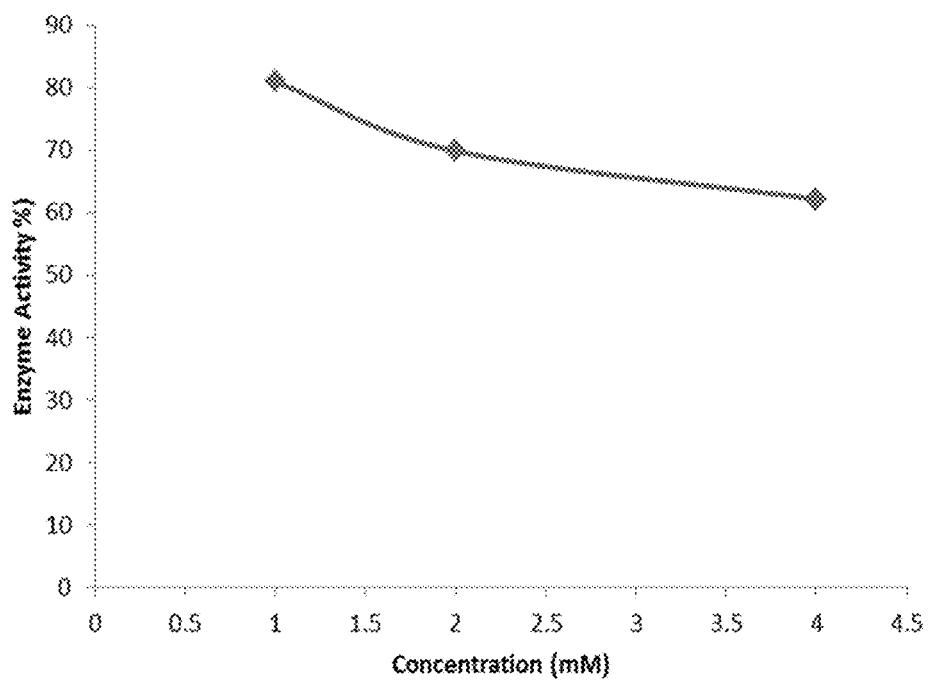
FIG. 5. Concentration Dependent Inhibition of Ala-AT by 1.
Figure 7:
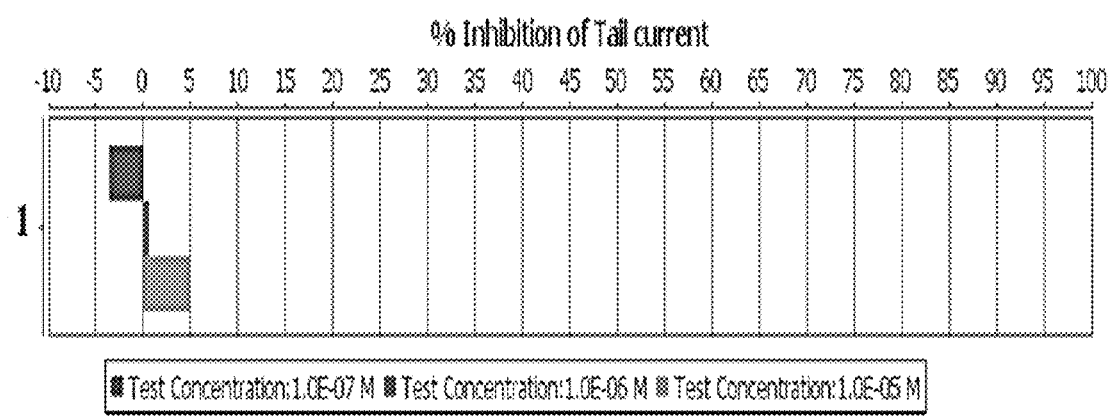
FIG. 7. Inhibition of the hERG Channel by 1 (hERG CHO-K1 cell line, detection method: automated patch-clamp): test concentration of 0E-7M, upper; 0E-6M, middle; and 0E-5M, lower.

Unlike vigabatrin, CPP-115 was reported not to inactivate or inhibit off-target enzymes, such as aspartate aminotransferase (Asp-AT) and alanine aminotransferase (Ala-AT), which could have contributed to its larger margin of safety than vigabatrin. Therefore, the activity of 1 was tested on these off-target enzymes. The results showed that 1 was a very weak reversible inhibitor of both Asp-AT and Ala-AT with an $IC_{50}$>4 mM (FIGS. 4 and 5). Another important PLP-dependent off-target enzyme is ornithine aminotransferase (OAT); high levels of OAT impair the detoxification of ammonia by ornithine carbamoyltransferase through the urea cycle. CPP-115 was reported to be a moderate inactivator of OAT with a $K_I$ value of 0.116 mM and a $k_{inact}$ value of 0.097 min$^{-1}$. Compound 1 also was shown to be a potent inactivator of OAT with a $K_I$ value of 0.0033 mM and a $k_{inact}$ value of 0.025 min$^{-1}$ (FIG. 6). By comparison of the $k_{inact}/K_I$ value of 1 (7.6 mM$^{-1}$ min$^{-1}$) with that of CPP-115 (0.84 mM$^{-1}$ min$^{-1}$), 1 is 9.0 times more efficient an inactivator of OAT than CPP-115, consistent with its higher efficiency as an inactivator of GABA-AT.

hERG is a potassium ion channel that contributes to the electrical activity of the heart, which coordinates the heart's beating. This channel is sensitive to drug binding, and when its ability to conduct electrical current across the cell membrane is compromised, it can result in potentially fatal cardiac adverse effects; therefore, it is important to avoid hERG inhibition during drug development. Like CPP-115, 1 does not inhibit the activity of the hERG channel (FIG. 7).

Figure 8:
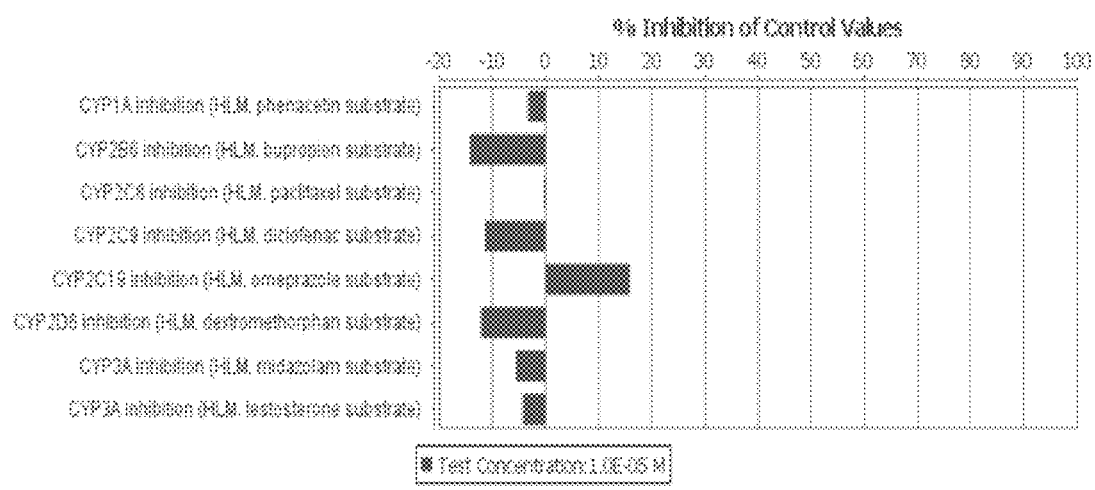
FIG. 8. Inhibition of Microsomal Cytochromes P450 by 1.

Microsomal cytochromes P450 (CYPs) are major enzymes that are involved in drug metabolism, accounting for ~75% of all drug metabolism. Thus, microsomal stability is often performed to predict if a drug will be eliminated too rapidly during drug development. Like CPP-115, 1 does not inhibit or induce the seven most common CYPs (1A, 2B6, 2C8, 2C9, 2C19, 2D6, and 3A) that are involved in ~95% of the reactions in drug metabolism (FIG. 8). Plasma protein binding is only 27%, indicating a high percentage of free drug in plasma.

Figure 9A:
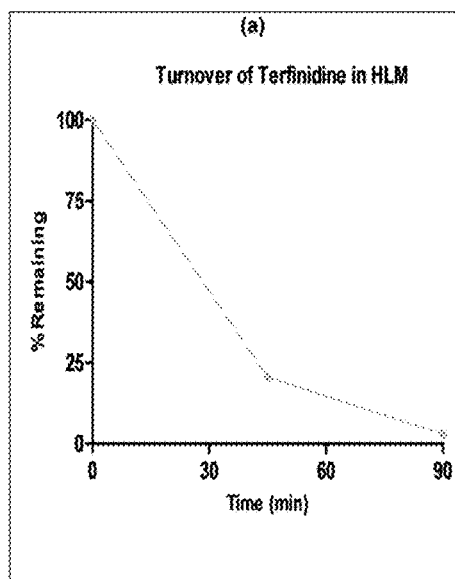
FIGS. 9A-B. Time-dependent Loss of (A) Terfenadine and (B) 1 in Human Liver Microsomes (HLM).
Figure 9B:
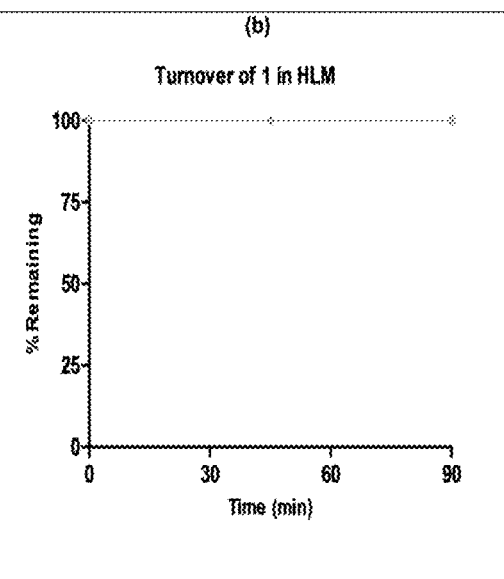

Compound 1 was also evaluated for its metabolic stability in human liver microsomes (HLM). This was accomplished by incubating 1 with the microsomes and monitoring its disappearance with time using LC-MS/MS. Terfenadine was run in similar condition as a positive control. The results showed that 1 was stable in HLM for 90 min (FIG. 9).

Drug addiction results from the release of dopamine in the NAcc when an addictive substance is ingested. The effect of 1 on the release of dopamine in freely moving rats was determined using in vivo micropositron emission tomography (microPET) imaging (FIG. 10). (Dewey, S. L.; Morgan, A. E.; Ashby, C. R.; Horan, B.; Kushner, S. A.; Logan, J.; Volkow, N. D.; Fowler, J. S.; Gardner, E. L.; Brodie, J. D. Synapse 1998, 30 (2), 119-129). In the central nervous system, especially the corpus striatum, where there is a high concentration of dopamine $D_2$ receptors (as seen by the two gray-shaded spots in the middle of each image in FIG. 10), [$_{11}$C]-raclopride competes with dopamine for the same receptor sites located on post-synaptic dopamine terminals. MicroPET was used to measure the dissociation of the tracer

[$^{11}$C]-raclopride from dopamine receptors caused by either cocaine- or nicotine-induced increases in synaptic dopamine levels (the same images were obtained with cocaine and nicotine). When animals received cocaine (n=8) or nicotine (n=6), striatal dopamine levels were rapidly elevated. (Dewey, S. L.; Chaurasia, C. S.; Chen, C. E.; Volkow, N. D.; Clarkson, F. A.; Porter, S. P.; Straughter-Moore, R. M.; Alexoff, D. L.; Tedeschi, D.; Russo, N. B.; Fowler, J. S.; Brodie, J. D. *Synapse* 1997, 25 (4), 393-398). These elevations effectively displaced [$^{11}$C]-raclopride from the receptors, as seen in FIG. 10B (middle frame; spots are much less gray-shaded). If the same animals (on a different day) received 1 prior to cocaine or nicotine, there was no change in [$^{11}$C]-raclopride binding (FIG. 10C, bottom frame); the degree of shading of the spots is equal to that of the controls (FIG. 10A, top frame), indicating that there was no increase in dopamine levels that would effectively compete with [$^{11}$C]-raclopride binding. Therefore, 1 blocks both cocaine- and nicotine-induced elevations in dopamine.

In addition to labeled raclopride studies, [$^{18}$F]-2'-fluoro-2'-deoxy-D-glucose ($^{18}$FDG) and microPET were also used to examine the regional effects of 1 on cocaine-induced increases in glucose metabolism. $^{18}$FDG is an analogue of glucose that gets taken up into neurons (or any cells in the human body) just like glucose. However, after $^{18}$FDG is phosphorylated, the corresponding 6'-phosphate cannot be further metabolized in the glycolytic pathway and remains in cells. Consequently, human PET studies have used $^{18}$FDG for decades to map the brain. For example, if an individual in a PET scanner performs a specific task with one hand while $^{18}$FDG is injected intravenously, neurons in the brain underlying that hand's ability to perform that task incorporate this radiolabeled sugar while other surrounding neurons do not. When a human or a rat receives a psychostimulant like cocaine, dopamine floods the synapse, causing postsynaptic neurons to fire frantically. Because this neuronal firing requires energy in the form of glucose, the result is that brain glucose metabolism increases in specific brain regions. The effect of 1 on cocaine-induced increases in glucose metabolism in freely moving rats was determined using statistical parametric mapping, in which all of the images from the cocaine-only animals were added together and then compared to the images obtained from the same animals that received 1 and cocaine. A statistical threshold (p<0.00001) was set, and a statistical parametric map, an image showing all the pixels that were statistically different between the two conditions, was generated and then overlaid on an MRI of the rat brain (FIG. 11). In the cocaine-only animals, an enormous activation in the hippocampus, a bilateral structure, was observed with one large gray spot on each side (FIG. 11A, left). In the cocaine/1 animals, the activation in the hippocampus was all gone (FIG. 11B, right). This is the largest attenuation by ingestion of a compound observed under this and related studies: Vigabatrin and CPP-115 previously went through similar tests; they both blocked cocaine-induced increases in striatal dopamine but did not completely block the hippocampal metabolism as 1 did.

Cocaine- and nicotine-induced increases in striatal dopamine are known to produce a conditioned place preference (CPP), which results in animals 'learning' to associate a specific environment with the drug they receive. When the striatum is activated by an elevation in dopamine levels (subsequent to a cocaine or nicotine challenge), projections to the hippocampi cause it to activate. The hippocampus plays a pivotal role in spatial memory; therefore, it is important for encoding environmental conditions during drug exposure. Because 1 blocked cocaine-induced increases in striatal dopamine, it is not surprising that it also inhibited increased metabolic demands in the hippocampus.

As can relate to various other embodiments of this invention, ornithine aminotransferase (OAT) belongs to the same evolutionary subgroup of PLP-dependent enzymes as GABA-AT. These two enzymes share a high structural homology and, like all aminotransferases, also have very similar catalytic mechanisms. As discussed more fully in co-pending application Ser. No. 14/936,153, OAT is expressed in many tissues, including liver, kidney, small intestine, brain, and eye and catalyzes the reversible conversion of ornithine and α-ketoglutarate to L-glutamate semialdehyde which cyclizes to $\Delta^1$-pyrroline-5-carboxylate and L-glutamate. L-glutamate is then converted by glutamine synthetase to L-glutamine.

Glutamine is the most abundant free amino acid in the body; it is essential for growth of both normal and neoplastic cells. However, tumor cells take up glutamine more efficiently than normal cells, and tumor growth is enhanced by glutamine. (See, e.g., Souba, W. W. Glutamine and cancer. *Ann. Surgery* 1993, 218, 715-728; Medina, M. A. Glutamine and cancer. *J. Nutr.* 2001, 131 (9 Supply, 2539S-2542S.) With respect to glutamine, cancer cells distinguish themselves from normal cells in that they have an increased requirement for glutamine to support anabolic processes that stimulate proliferation. (The aforementioned '153 application, filed Nov. 9, 2015, is incorporated herein by reference in its entirety.)

Because of the structural similarities between OAT and GABA-AT, it has been shown that some inactivators of GABA-AT also inactivate OAT. As demonstrated below, compounds of this invention can also be used to modulate, reduce and/or inhibit OAT activity. More specifically, methodologies and protocols detailed in the aforementioned, incorporated '153 application can be employed to show such compounds as useful in the treatment of malignant pathologic proliferative disorders, including but not limited to hepatocellular carcinoma.

As can relate to various other embodiments of this invention, GABA-AT inhibitors have been shown to be effective for treatment of psychological disorders including but not limited to general anxiety disorder, pathological or compulsive gambling disorder, compulsive eating (obesity), body dysmorphic disorder, hypochondriasis, pathologic grooming conditions, kleptomania, pyromania, attention deficit hyperactivity disorder and impulse control disorders and neurological disorders including but not limited to epilepsy, infantile spasms, epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathy, migraines related to epilepsy, restless leg syndrome, post traumatic distress disorder and Alzheimer's disease and combinations thereof, such treatments as are described in U.S. Pat. No. 8,969,413, the entirety of which is incorporated herein by reference. Accordingly, compounds of this invention can also be used to treat such disorders. More specifically, methodologies and protocols detailed and incorporated into the '413 patent can be employed to show such compounds as useful in the treatment of neurological and psychological disorders, including but not limited to those described, above.

Methods of the present invention can also, as would be understood by those skilled in the art, be extended to or include methods using or in conjunction with a pharmaceutical composition comprising a compound of the sort described herein and a physiologically or otherwise suitable formulation. In some embodiments, the present invention includes one or more GABA-AT or OAT inactivator compounds, as set forth above, formulated into compositions together with one or more physiologically tolerable or acceptable diluents, carriers, adjuvants or vehicles that are collectively referred to herein as carriers. Compositions suitable for such contact or administration can comprise physiologically acceptable sterile aqueous or nonaqueous solutions, dispersions, suspensions or emulsions. The resulting compositions can be, in conjunction with the various methods described herein, for administration or contact with a cellular medium and/or a GABA-AT or OAT expressed or otherwise present therein. Whether or not in conjunction with a pharmaceutical composition, "contacting" means that a GABA-AT or OAT and one or more inactivator compounds are brought together for purpose of binding and/or complexing such an inactivator compound to the enzyme. Amounts of a compound effective to such an aminotransferase may be determined empirically, and making such determinations is within the skill in the art. Modulation, inhibition or otherwise affecting GABA-AT or OAT activity includes both reduction and/or mitigation, as well as elimination of GABA-AT activity and/or dopamine release or, alternatively, both reduction and/or mitigation, as well as elimination of OAT activity, glutamate production, cell proliferation and/or tumor growth.

It is understood by those skilled in the art that dosage amount will vary with the activity of a particular inactivator compound, disease state, route of administration, duration of treatment, and like factors well-known in the medical and pharmaceutical arts. In general, a suitable dose will be an amount which is the lowest dose effective to produce a therapeutic or prophylactic effect. If desired, an effective dose of such a compound, pharmaceutically-acceptable salt thereof, or related composition may be administered in two or more sub-doses, administered separately over an appropriate period of time.

Methods of preparing pharmaceutical formulations or compositions include the step of bringing one or more inactivator compounds into association with a carrier and, optionally, one or more additional adjuvants or ingredients. For example, standard pharmaceutical formulation techniques can be employed, such as those described in Remington's Pharmaceutical Sciences, Mack Publishing Company, Easton, Pa.

Regardless of composition or formulation, those skilled in the art will recognize various avenues for medicament administration, together with corresponding factors and parameters to be considered in rendering such a medicament suitable for administration. Accordingly, with respect to one or more non-limiting embodiments, the present invention provides for use of one or more inactivator compounds for the manufacture of a medicament for therapeutic use in the treatment of various disease states, in particular with respect to GABA-AT, the treatment of neurological and psychological disorders, including addictions and substance addictions, and associated indications or, with respect to OAT, the treatment of hepatocellular carcinoma or the prevention thereof.

EXAMPLES OF THE INVENTION

The following non-limiting examples and data illustrate various aspects and features relating to the compounds/compositions and/or methods of the present invention, including various GABA-AT and/or OAT inactivator compounds, as are available through the synthetic methodology described herein. In comparison with the prior art, the present compounds and methods provide results and data which are surprising, unexpected and contrary thereto. While the utility of this invention is illustrated through the use of several compounds and substituents which can be incorporated therein, it will be understood by those skilled in the art that comparable results are obtainable with various other compounds and substituents, as are commensurate with the scope of this invention.

General Procedures

CPP-115 was synthesized at IRIX Pharmaceuticals for Catalyst Pharmaceuticals, which generously provided it; other chemicals were obtained from Sigma-Aldrich and used as received unless specified. All syntheses were conducted under anhydrous conditions in an atmosphere of argon, using flame-dried apparatus and employing standard techniques in handling air-sensitive materials, unless otherwise noted. All solvents were distilled and stored under an argon or nitrogen atmosphere before use. $^1$H NMR and $^{13}$C NMR spectra were taken on a Bruker AVANCE III 500 spectrometer, an Agilent DDR2 400 MHz spectrometer, or an Agilent DD2 500 MHz spectrometer with an Agilent 5 mm HFX probe at 26° C. using DMSO-$d_6$ or $D_2O$ as solvents, recorded in δ (ppm) and referenced to DMSO-$d_6$ (2.50 ppm for $^1$H NMR and 39.52 ppm for $^{13}$C NMR) or $D_2O$ (4.79 ppm for $^1$H NMR). High resolution mass spectra (HRMS) were measured with an Agilent 6210 LC-TOF (ESI, APCI, APPI) mass spectrometer.

Example 1

Methyl (1S,3S)-3-((tert-butoxycarbonyl)amino)-4-(difluoromethylenyl)cyclopentane-1-carboxylate (3). To dry methanol (27 mL) was added acetyl chloride (2.49 mL, 35 mmol) at 0° C. and stirred for 10 min. To the resulting solution was added CPP-115 hydrochloride salt (1, 1.5 g, 7.0 mmol) and stirred for 24 h at room temperature. Triethylamine (6.8 mL, 49 mmol) and di-tert-butyl dicarbonate (1.9 mL, 8.4 mmol) were then added, and the resulting solution was stirred for 20 h at room temperature. The reaction mixture was concentrated and redissolved in ethyl acetate. The organic solution was washed with 2 N HCl, saturated $NaHCO_3$, and brine. The organic layer was dried over $Na_2SO_4$, followed by filtration and evaporation to afford 3 (1.99 g, 6.83 mmol, 97%) as a white solid; $^1$H NMR (500 MHz, 60° C., DMSO-$d_6$) δ 6.89 (s, 1H), 4.57 (s, 1H), 3.63 (s, 3H), 2.86 (m, 1H), 2.55-2.51 (m, 1H), 2.23 (ddt, J=10.0, 7.1, 2.9 Hz, 1H), 1.79 (m, 1H), 1.39 (s, 9H); $^{13}$C NMR (126 MHz, 60° C., DMSO-$d_6$) δ 173.74, 154.78, 152.80, 150.54, 148.27, 92.12, 91.98, 91.84, 77.86, 51.72, 49.45, 40.31, 36.51, 28.31, 28.16; $^{19}$F NMR (470 MHz, 60° C., DMSO-$d_6$) δ −89.49 (d, J=55.9 Hz), −92.89 (d, J=57.7 Hz); HRMS (M+Na$^+$) calcd for $C_{13}H_{19}F_2NNaO_4$ 314.1174, found 314.1179.

Example 2

Methyl (3S)-3-((tert-butoxycarbonyl)amino)-4-(difluoromethylenyl)-1-(phenylselanyl)cyclopentane-1-carboxylate (4). To a solution of KHMDS (14.96 mL of 1M solution in THF, 14.96 mmol) and dry THF (10 mL) at −78° C. was added a solution of 3 (1.98 g, 6.80 mmol) in dry THF (10 mL) slowly via syringe. The reaction mixture was stirred at −78° C. for 90 min. A solution of phenylselenyl chloride (1.43 g, 7.48 mmol) in dry THF (2 mL) was added and stirring was continued at −78° C. for 75 min. The reaction mixture was then allowed to warm to 0° C., stirred at 0° C. for 3 h, warmed to room temperature, and stirred at room temperature for 2 h. Saturated aqueous ammonium chloride and ethyl acetate were added. The organic layer was washed with saturated aqueous ammonium chloride and dried over $Na_2SO_4$. Filtration and evaporation gave a crude mixture, which was purified by silica gel column chromatography (hexane/EtOAc) to afford a 5:2 diastereomeric mixture (4, 2.12 g, 4.75 mmol, 70%) as a pale brown syrup; $^1$H NMR (500 MHz, 60° C., DMSO-$d_6$) δ 7.58-7.37 (m, 5H), 6.97 (s, 1H), 4.83 (s, 0.7H), 4.47 (s, 0.3H), 3.64 (s, 2.2H), 3.57 (s, 0.8H), 2.96-2.88 (m, 1H), 2.68-2.63 (m, 0.7H), 2.43-2.36 (m, 0.7H), 2.23-2.14 (m, 1.3H), 2.00-1.95 (m, 0.3H), 1.39 (s, 9H); $^{13}$C NMR (126 MHz, DMSO-$d_6$) δ 172.09, 171.96, 154.41, 153.76, 151.48, 150.64, 149.21, 136.79, 136.76, 129.48, 129.28, 128.91, 128.84, 126.53, 126.20, 91.00, 90.91, 90.85, 90.76, 90.70, 90.61, 77.88, 59.38, 52.11, 51.85, 51.84, 50.01, 48.64, 42.72, 40.67, 35.76, 34.17, 34.15, 27.90, 27.55; $^{19}$F NMR (470 MHz, 60° C., DMSO-$d_6$) δ −88.29 (d, J=51.2 Hz), −89.34 (d, J=52.9 Hz), −91.00 (d, J=54.8 Hz); HRMS (M+Na$^+$) calcd for $C_{19}H_{23}F_2NNaO_4Se$ 470.0654. found 470.0660 (the most abundant Se isotope was picked).

Example 3

(3S)-3-((tert-Butoxycarbonyl)amino)-4-(difluoromethylenyl)-1-(phenylselanyl)cyclopentane-1-carboxylic acid (5). To a solution of 4 (1.40 g, 3.13 mmol) in methanol (14 mL) and water (4 mL) at 0° C. was added lithium hydroxide (225 mg, 9.39 mmol). The reaction mixture was allowed to warm to room temperature and was stirred for 20 h. Ethyl acetate was added and the organic solution was washed with 10% citric acid and brine. The organic layer was then dried over $Na_2SO_4$, filtered, and concentrated. The crude mixture was subjected to silica gel column chromatography (hexane/ethyl acetate) to afford 5 (1.25 g, 2.89 mmol, 92%) as a white powder. $^1$H NMR (500 MHz, 60° C., DMSO-$d_6$) δ 12.61 (s, 1H), 7.64-7.54 (m, 2H), 7.46-7.42 (m, 1H), 7.41-7.35 (m, 2H), 6.94 (s, 1H), 4.81 (s, 0.7H), 4.48 (s, 0.3H), 2.97-2.83 (m, 1H), 2.67-2.56 (m, 0.7H), 2.35 (dd, J=16.9, 2.7 Hz, 0.7H), 2.20-2.10 (m, 1.3H), 1.91 (dd, J=12.9, 8.3 Hz, 0.3H), 1.42-1.35 (m, 9H); $^{13}$C NMR (126 MHz, DMSO-$d_6$) δ 173.76, 173.56, 154.71, 154.64, 153.93, 151.65, 150.69, 149.38, 136.87, 136.81, 129.60, 129.39, 129.20, 129.14, 127.06, 126.55, 91.67, 91.52, 91.40, 91.37, 91.26, 91.11, 78.06, 52.38, 49.99, 48.69, 48.42, 42.95, 40.68, 36.08, 34.26, 28.15; $^{19}$F NMR (470 MHz, 60° C., DMSO-$d_6$) δ −88.52 (d, J=52.9 Hz), −89.53 (d, J=53.2 Hz), −91.25 (d, J=53.2 Hz), −91.45 (d, J=55.3 Hz); HRMS (M+Na$^+$) calcd for $C_{18}H_{21}F_2NNaO_4Se$ 456.0502. found 456.0498 (the most abundant Se isotope was selected).

Example 4

(3S)-3-Amino-4-(difluoromethylenyl)-1-(phenylselanyl)cyclopentane-1-carboxylic acid (6). To a solution of 5 (1.31 g, 3.03 mmol) in $CH_2Cl_2$ (13 mL) at 0° C. was added trifluoroacetic acid (3.2 mL) and the reaction was stirred for 4 h at the same temperature. The mixture was concentrated and dried in vacuo. The crude residue was subjected to cation exchange column chromatography (Dowex 50W-X8, 5% aqueous pyridine as a eluent) to afford 6 (990 mg, 2.98 mmol, 98%) as an off-white solid. $^1$HNMR (500 MHz, $D_2O$) δ 7.70-7.63 (m, 2H), 7.53-7.46 (m, 1H), 7.45-7.40 (m, 2H), 4.61 (t, J=6.7 Hz, 0.7H), 4.44 (m, 0.3H), 3.02-2.84 (m, 1.3H), 2.71-2.57 (m, 1H), 2.49 (dd, J=14.7, 7.8 Hz, 0.7H), 2.29 (dd, J=14.7, 7.4 Hz, 0.7H), 2.09 (dd, J=14.4, 5.3 Hz, 0.3H); $^{13}$C NMR (126 MHz, $D_2O$) δ 182.36, 181.63, 158.52, 158.05, 156.23, 155.76, 153.93, 153.46, 140.18, 139.99, 132.61, 132.55, 132.25, 132.20, 129.96, 129.65, 91.48, 91.42, 91.33, 91.26, 91.22, 91.13, 91.07, 60.00, 58.39, 52.13, 52.09, 52.03, 44.28, 43.38, 38.91, 38.30; $^{19}$F NMR (470 MHz, $D_2O$) δ −84.06 (d, J=42.6 Hz), −84.38--84.58 (m), −84.72 (ddd, J=45.2, 4.5, 2.4 Hz), −85.08 (ddd, J=44.6, 5.8, 2.7 Hz); HRMS (M+H$^+$) calcd for $C_{13}H_{14}F_2NO_2Se$ 334.0158. found 334.0155 (the most abundant Se isotope was selected).

Example 5

(S)-3-Amino-4-(difluoromethylenyl)cyclopent-1-ene-1-carboxylic acid Hydrochloride (1). To the solution of 6 (100 mg, 0.30 mmol) and $NaHCO_3$ (55 mg, 0.66 mmol) in water (2 mL) at 0° C. was added sodium periodate (71 mg, 0.33 mmol). The reaction mixture was allowed to warm to room temperature and stirred for 6 h. The reaction mixture was directly applied to a cation exchange column (Dowex 50W-X8, 2 N HCl as an eluent) to afford a crude mixture. The crude mixture was subjected to C-18 reverse phase column chromatography (water/methanol) to afford a mixture of 1 and 2 (62 mg, 0.29 mmol, 96%) as a white powder (Note: an aliquot of 2 N HCl was added when concentrating the sample to make sure the solution was strongly acidic). To a solution of the mixture of 1 and 2 (51 mg, 0.24 mmol) in methanol (2 mL) and water (0.5 mL) at 0° C. was added thiosalicylic acid (112 mg, 0.72 mmol). The reaction mixture was allowed to warm to room temperature and stirred for 5 h. After the reaction was confirmed complete by $^{19}$F NMR, the reaction mixture was concentrated and water added. The suspension was filtered through a cotton plug, and the filtrate was subjected to C-18 reverse phase column chromatography (water/methanol) to afford 1 (23 mg, 0.11 mmol, 76% from the content of 1 in the previous isomeric mixtures) as a white powder; $^1$H NMR (500 MHz, $D_2O$) δ 6.29 (s, 1H), 5.16 (s, 1H), 3.37 (m, 2H); $^{13}$C NMR (126 MHz, $D_2O$) δ 174.42, 158.05, 155.76, 153.46, 150.08, 132.06, 89.80, 89.64, 89.59, 89.43, 57.84, 57.79, 34.85; $^{19}$F NMR (376 MHz, $D_2O$) δ −83.86 (ddd, J=42.8, 6.0, 3.2 Hz), −84.12 (ddd, J=43.0 4.9, 2.7 Hz); HRMS (M−H$^-$) calcd for $C_7H_6F_2NO_2$ 174.0372, found 174.0374; HPLC purity (100% by UV absorbance at 210 nm, 100% by ELSD).

Example 6

Analysis of Sample Purity by HPLC.

An Agilent 1260 infinity HPLC system was used, which consisted of a variable wavelength detector (G1314A), a thermostatted column compartment (G1316A), an autosampler (G1329B), an evaporative light scattering detector (ELSD, G4261A), a quaternary pump (G1311B), and a C-18 reverse phase column (Agilent Poroshell 120, 2.7 μm, 4.6 mm×50 mm). The experiments were run with 5 μL (0.5 mg/mL in water) injections, and sample elution was monitored by UV absorbance at 210 nm and by ELSD in a linear gradient experiment (water/acetonitrile with 0.05% trifluoroacetic acid, gradient system: from initial 2% acetonitrile to 100% acetonitrile in 7 min, then 100% acetonitrile for 3 min).

Example 7

Molecular Modeling.

All renderings were performed in PyMol. (Koo, Y. K.; Nandi, D.; Silverman, R. B. *Arch. Biochem. Biophys.* 2000, 374 (2), 248 254.) Computer simulations were carried out as previously described. (Silverman, R. B.; Bichler, K. A.; Leon, A. J. *J. Am. Chem. Soc.* 1996, 118 (6), 1241 1252.) In short, the ligands (as adducts with the cofactor) were prepared using the R.E.D. server and transformed into topology files using the Antechamber module of the AMBER program. (Yuan, H.; Silverman, R. B. *Bioorganic Med. Chem.* 2006, 14 (5), 1331-1338.) The non-tautomerized molecules were then docked into the active site of GABA-AT (prepared from pdb entry #1OHW) using Autodock 4.2, with Lys329 as a flexible sidechain. The best docked structures were then refined by molecular mechanics, using GROMACS 4.5. The sequence involved energy minimization, molecular dynamics (4 ns), and a final energy minimization. At this stage, structures were tautomerized in place, and the molecular mechanics sequence was performed again. The final output structures were used for evaluation without further refinement.

Example 8

Enzyme and Assays.

GABA-AT (1.48 mg/mL) was purified from pig brain by a procedure described previously. (Koo, Y. K.; Nandi, D.; Silverman, R. B. *Arch. Biochem. Biophys.* 2000, 374 (2), 248 254.) Succinic semialdehyde dehydrogenase (SSDH) was purified from GABase, a commercially available mixture of SSDH and GABA-AT, using a known procedure. (Silverman, R. B.; Bichler, K. A.; Leon, A. J. *J. Am. Chem. Soc.* 1996, 118 (6), 1241 1252.) GABA-AT activity was assayed using a published method. (Scott, E. M.; Jakoby, W. B. *J. Biol. Chem.* 1959, 234 (4), 932-936.) GABase (*Pseudomonas fluorescens*) and succinic semialdehyde were purchased from Sigma-Aldrich. The final assay solution consisted of 10 mM GABA, 1.2 mM NADP+, 5 mM α-ketoglutarate, 5 mM β-mercaptoethanol, and excess SSDH in 50 mM potassium pyrophosphate buffer, pH 8.5. The change in UV absorbance at 340 nm at 25° C. caused by the conversion of NADP+ to NADPH was monitored. The enzyme assays for the determination of $k_{inact}$ and $K_I$ values were recorded with a Shimadzu UV-1800 UV/Vis spectrophotometer, using a 1 mm width, 10 mm path length, 45 mm height micro quarts cuvette. The enzyme assays for the GABA-AT inactivation and dialysis experiment were recorded with a BioTek Synergy H1 microplate reader.

Example 9

Determination of the $k_{inact}$ and $K_I$ Values.

The activity of the GABA-AT was measured under the conditions described in the Enzyme and Assay section in the presence of different concentrations of inactivators, ranging from 1 to 200 μM for 1, and from 50 to 1600 μM for CPP-115. The curves of GABA-AT activity caused by inactivation were fitted to equation (1) using GraphPad Prism 6™ software to afford the $k_{obs}$ values at each inactivator concentration.

$$\text{Absorbance} = \frac{v_i - v_s}{k_{obs}}[1 - \exp(-k_{obs}t)] + v_s t + a_0 \quad \text{Equation (1)}$$

where $v_i$ is the initial velocity, $v_s$ is the steady state velocity, t is time, $a_0$ is the initial absorbance and $k_{obs}$ is the observed rate of inactivation. (Salminen, K. A.; Leppänen, J.; Venäläinen, J. I.; Pasanen, M.; Auriola, S.; Juvonen, R. O.; Raunio, H. *Drug Metab. Dispos.* 2011, 39 (3), 412-418.) The $k_{obs}$ values were plotted against concentrations of the compound, and the best fit curve was then fitted into equation (2) to afford $K_I$ and $k_{inact}$ values.

$$k_{obs} = \frac{k_{inact}(I)}{K_I\left(1 + \frac{S}{K_m}\right) + [I]} \quad \text{Equation (2)}$$

where [I] is the inactivator concentration, S is the substrate (GABA) concentration applied, $K_m$ is the Michaelis-Menten constant of the substrate (GABA). The $K_m$ value of GABA with GABA-AT used for the calculation was 1.3 mM. (Yuan, H.; Silverman, R. B. *Bioorganic Med. Chem.* 2006, 14 (5), 1331-1338.)

Example 10

Inactivation of GABA-AT by 1, and Dialysis of the Inactivated Enzyme.

The dialysis experiment was conducted following a previously reported procedure. (Lee, H.; Doud, E. H.; Wu, R.; Sanishvili, R.; Juncosa, J. I.; Liu, D.; Kelleher, N. L.; Silverman, R. B. *J. Am. Chem. Soc.* 2015, 137 (7), 2628-2640.) To the GABA-AT buffer (0.148 mg/mL, 30 μL) was added 50 μL of the 16 μM inactivator buffer solution (50 mM potassium pyrophosphate, pH 8.5, 5 mM α-ketoglutarate, 5 mM β-mercaptoethanol) so that the final concentration of GABA-AT and the inactivator would be 1 and 10 μM, respectively. In another experiment as a control reference, the same amount of the GABA-AT buffer solution without the inactivator was prepared. The sample solutions were incubated for 4 h at room temperature in the dark. The remaining enzyme activity was measured by taking 5 μL from the solution. The inactivated and the control GABA-AT solution were transferred to a D-Tube™ Dialyzer Mini (MWCO 12-14 kDa) and dialyzed against the dialysis buffer (350 mL, 50 mM potassium pyrophosphate, pH 8.5, 0.1 mM α-ketoglutarate, 0.1 mM pyridoxal 5'-phosphate) at 4° C. The dialysis buffer was exchanged three times at 4, 8, and 24 h. The enzyme activity was measured at 4, 8, 24, 48, and 72 h.

Example 11

Inhibition of Aspartate Aminotransferase by 1.

Microtiter plate wells were loaded with 90 μL of an assay mixture containing 100 mM potassium phosphate at pH 7.4, 5.55 mM α-ketoglutarate, 1.11 mM NADH, 5.55 mM L-aspartate, 11.1 units of malic dehydrogenase, and various concentrations of 1. After incubation of the mixture at room temperature for a few min, 10 μL of Asp-AT (3.0 units/mL in 100 mM potassium phosphate at pH 7.4) was added. The plate was shaken at room temperature for 1 min, and the absorbance was measured at 340 nm every 6 s for 90 min. All assays were performed in duplicate (FIG. 4).

Example 12

Inhibition of Alanine Aminotransferase by 1.

The assay was identical to that with aspartate aminotransferase except L-alanine was used as the substrate and lactate dehydrogenase was the enzyme (FIG. 5).

Example 13

Time- and Concentration-Dependent Inhibition of Ornithine Aminotransferase by 1.

These assays were performed using a modification of the procedure by Juncosa, Lee and Silverman. OAT (0.25 µg) was incubated with various concentrations of 1 (0.5 µM, 2 µM, 5 µM, 10 µM, 20 µM) in 100 mM potassium pyrophosphate buffer, pH 8.0, containing 1 mM α-ketoglutarate in a total volume of 20 µL at room temperature. At time intervals, 80 µL of assay solution, preincubated at 37° C. for 10 min, containing PYCR1 (0.5 µg), 12.5 mM α-ketoglutarate, 1 mM NADH, 0.03 mM PLP, and 25 mM L-ornithine in 100 mM potassium pyrophosphate buffer, pH 8.0, was added to the incubation mixture and assayed for OAT activity at 37° C. for 20 min. All assays were performed in duplicate, and the remaining OAT activity at each preincubation time at each inhibitor concentration was averaged. The natural logarithm of the percentage of the remaining OAT activity was plotted against the preincubation time at each inhibitor concentration to obtain the $k_{obs}$ (slope) value for each concentration. The $k_{obs}$ is the rate constant describing the inactivation at each inhibitor concentration. $k_{obs}$ is replotted against the inhibitor concentration using nonlinear regression analysis (GraphPad Prism 6™; GraphPad Software Inc.). $K_I$ and $k_{inact}$ were estimated from equation (3):

$$k_{obs} = \frac{k_{inact} \times [I]}{K_I + [I]} \quad \text{Equation 3}$$

where $k_{inact}$ is the maximal rate of inactivation, $K_I$ is the inhibitor concentration required for half-maximal inactivation, and [I] is the preincubation concentration of 1 (FIG. 6).

Example 14

Inhibition of the hERG Channel.

The experiments were performed by Eurofins Panlabs (Redmond, Wash. 98052, USA). hERG CHO-K1 cell line was used. The test concentrations were 0.1 µM, 1 µM, and 10 µM. The incubation time was 5 min at room temperature, cumulatively. The detection method used an automated whole-cell patch clamp. The experiments were duplicated, and the % inhibition of the tail current was averaged (FIG. 7).

Example 15

Inhibition of Microsomal Cytochromes P450.

The experiments were performed by Eurofins Panlabs (Redmond, Wash. 98052, USA). CYP1A inhibition (HLM, phenacetin substrate), CYP2B6 inhibition (HLM, bupropion substrate), CYP2C8 inhibition (HLM, paclitaxel substrate), CYP2C9 inhibition (HLM, diclofenac substrate), CYP2C19 inhibition (HLM, omeprazole substrate), CYP2D6 inhibition (HLM, dextromethorphan substrate), and CYP3A inhibition (HLM, midazolam and testosterone substrates) were tested. The test concentration was 10 µM. The incubation time was 10 min at 37° C. The detection method was by HPLC-MS/MS. The experiments were duplicated, and the % inhibition of the control values was averaged (FIG. 8).

Example 16

MicroPET Imaging.

Adult male rats (Sprague-Dawley, 200-250 grams, n=16) were obtained from Taconic Farms. Animals were maintained on a 12/12 light-dark cycle. Scanning was performed using a Siemen's Inveon. All emission scans were corrected for attenuation. Animals received baseline microPET scans using either $^{11}$C-raclopride or $^{18}$FDG as described previously. (Patel, V. D.; Lee, D. E.; Alexoff, D. L.; Dewey, S. L.; Schiffer, W. K. *Neuroimage* 2008, 41 (3), 1051-1066.) Uptake of both radiotracers occurred while animals were awake and freely moving. Immediately prior to microPET scanning, all animals were anesthetized and maintained under isoflurane.

As demonstrated, the present invention provides potent GABA-AT inactivators. In vitro results show, in particular, that 1 is 9.8 times more efficient an inactivator of GABA-AT than CPP-115, currently the most potent GABA-AT inactivator, which has high therapeutic potential as a treatment for cocaine addiction. In vivo studies in freely moving rats showed that 1 is superior to CPP-115 in suppressing the release of dopamine in the NAcc following a cocaine or nicotine challenge. Compound 1 also attenuated dopamine-induced increases in metabolic demand within the hippocampus, a brain region previously demonstrated to encode spatial conditions of the environment associated with drug-induced increases in dopamine.

We claim:

1. A compound of a formula

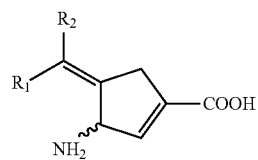

wherein each of $R_1$ and $R_2$ is independently selected from H, F, Cl, Br and I, providing at least one of $R_1$ and $R_2$ is not H, or a salt thereof.

2. The compound of claim 1 wherein said amino substituent has an (S) stereochemical configuration.

3. The compound of claim 2 wherein at least one of $R_1$ and $R_2$ is F.

4. The compound of claim 1 wherein said compound is a salt comprising a substituent selected from an ammonio substituent, a carboxylate substituent and a combination thereof.

5. The compound of claim 4, wherein the salt is an ammonium salt and said ammonium salt has a counter ion that is the conjugate base of a protic acid.

6. A pharmaceutical composition comprising the compound of claim 1 and a pharmaceutically-acceptable carrier component.

7. A compound of a formula

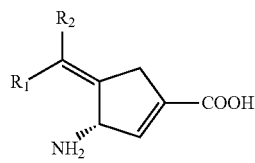

wherein each of $R_1$ and $R_2$ is independently selected from H and F, provided at least one of $R_1$ and $R_2$ is F, or a salt thereof.

8. The compound of claim 7 wherein each of $R_1$ and $R_2$ is F.

9. The compound of claim 7 wherein said compound is a salt comprising a substituent selected from an ammonio substituent, a carboxylate substituent and a combination thereof.

10. The compound of claim 9 wherein the salt is an ammonium salt and said ammonium salt has a counter ion that is the conjugate base of a protic acid.

11. A pharmaceutical composition comprising the compound of claim 7 and a pharmaceutically-acceptable carrier component.

12. A method of modulating GABA-AT activity, said method comprising:
providing a compound of a formula

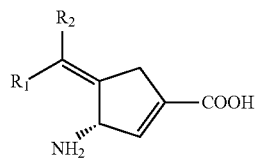

wherein each of $R_1$ and $R_2$ is independently selected from H, F, Cl, Br and I, providing at least one of $R_1$ and $R_2$ is not H, or a salt thereof; and
contacting said compound with a medium comprising a γ-aminobutyric acid aminotransferase, said compound in an amount sufficient to modulate γ-aminobutyric acid aminotransferase activity.

13. The method of claim 12 wherein at least one of $R_1$ and $R_2$ is F.

14. The method of claim 12 wherein said compound is a salt comprising a substituent selected from an ammonio substituent, a carboxylate substituent and a combination thereof.

15. The method of claim 14 wherein the salt is an ammonium salt and said ammonium salt has a counter ion that is the conjugate base of a protic acid.

16. The method of claim 12 wherein said contact is in vivo.

17. A method of modulating dopamine levels responsive to ingestion of an addictive substance, said method comprising:
providing a compound of claim 7; and
contacting said compound with a cellular medium comprising a γ-aminobutyric acid aminotransferase, said compound in an amount sufficient to modulate dopamine levels responsive to ingestion of an addictive substance, thereby increasing γ-aminobutyric acid levels in said medium.

18. The method of claim 17 wherein each of $R_1$ and $R_2$ is F.

19. The method of claim 17 wherein said compound is a salt comprising a substituent selected from an ammonio substituent, a carboxylate substituent and a combination thereof.

20. The method of claim 19 wherein the salt is an ammonium salt and said ammonium salt has a counter ion that is the conjugate base of a protic acid.

21. The method of claim 17 wherein said contact is with a mammalian subject comprising said cellular medium.

22. The method of claim 21 providing treatment of excessive dopamine release in a mammalian subject in need thereof.

23. A method for treatment of substance addiction, said method comprising administering to a mammalian subject in need thereof a compound of claim 7, said compound in an amount sufficient to increase γ-aminobutyric acid levels and modulate dopamine levels in the hippocampus of said subject, thereby reducing glucose metabolism in said hippocampus.

24. The method of claim 23 wherein each of $R_1$ and $R_2$ is F.

25. The method of claim 23 wherein said compound is a salt comprising a substituent selected from an ammonio substituent, a carboxylate substituent and a combination thereof.

26. The method of claim 25 wherein the salt is an ammonium salt and said ammonium salt has a counter ion that is the conjugate base of a protic acid.

27. The method of claim 23 providing treatment of said subject for at least one of cocaine, heroin, alcohol, barbiturates, amphetamines, cannabis, methadone, opioids, stimulants and nicotine addiction.

28. A method of modulating ornithine aminotransferase activity, said method comprising:
providing a compound of a formula

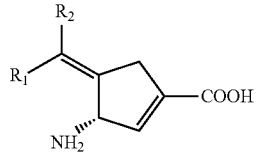

wherein each of $R_1$ and $R_2$ is independently selected from H, F, Cl and Br, providing at least one of $R_1$ and $R_2$ is not H, or a salt thereof; and
contacting said compound with a medium comprising an ornithine aminotransferase, said compound in an amount sufficient to modulate ornithine aminotransferase activity.

29. The method of claim 28 wherein at least one of $R_1$ and $R_2$ is F.

30. The method of claim 28 wherein said compound is a salt comprising a substituent selected from an ammonio substituent, a carboxylate substituent and a combination thereof.

31. The method of claim 30 wherein the salt is an ammonium salt and said ammonium salt has a counter ion that is the conjugate base of a protic acid.

32. The method of claim 28 wherein said contact is in vivo.

33. A method of reducing activity of an ornithine aminotransferase expressed by a human hepatocellular carcinoma, said method comprising:

providing a compound of a formula

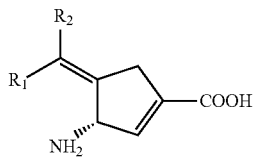

wherein $R_1$ and $R_2$ are selected from H and F, and at least one of $R_1$ and $R_2$ is F; or a salt thereof; and
  contacting a cellular medium comprising a hepatocellular carcinoma expressing an ornithine aminotransferase with an amount of said compound effective to reduce ornithine aminotransferase activity, thereby reducing glutamate production in said cellular medium.

34. The method of claim 33 wherein each of R1 and R2 is F.

35. The method of claim 34 wherein said compound is provided in a pharmaceutical composition.

36. The method of claim 34 wherein such contact is in vivo.

37. The method of claim 36 wherein said contact is with a human subject in need thereof.

38. A method for treatment of psychological and neurological disorders, said method comprising administering to a mammalian subject in need thereof a compound of claim 7, said compound in an amount sufficient to increase γ-aminobutyric acid levels in said subject.

39. The method of claim 38 wherein said neurological disorder is selected from epilepsy, partial seizures, complex partial seizures, secondary generalized seizures, tonic-clonic seizures, succinic semialdehyde dehydrogenase deficiency (SSADHD), infantile spasms in West's syndrome, Lennox-Gastaut syndrome, tubulous sclerosis, Tourette's syndrome, movement disorders, fibromyalgia, neuropathic pain, migraine related to epilepsy, restless leg syndrome and post traumatic stress disorder, addiction, obesity, obsessive-compulsive disorders and Alzheimer's disease and combinations thereof.

40. The method of claim 38 wherein said psychological disorder selected from general anxiety disorder, pathological or compulsive gambling disorder, compulsive eating, body dysmorphic disorder, hypochondriasis, pathologic grooming conditions, kleptomania, pyromania, attention deficit hyperactivity disorder and impulse control disorders and combinations thereof.

41. The method of claim 38 wherein each of R1 and R2 is F.

42. The method of claim 38 wherein said compound is provided in a pharmaceutical composition.

* * * * *